(12) United States Patent
Nyman et al.

(10) Patent No.: US 10,245,109 B2
(45) Date of Patent: Apr. 2, 2019

(54) STEREOTACTIC SURGICAL INSTRUMENT

(71) Applicant: ELEKTA AB (PUBL), Stockholm (SE)

(72) Inventors: Markus Nyman, Stockholm (SE); Erik Rurling, Stockholm (SE)

(73) Assignee: ELEKTA AB (PUBL), Stockholm (SE)

( * ) Notice: Subject to any disclaimer, the term of this patent is extended or adjusted under 35 U.S.C. 154(b) by 412 days.

(21) Appl. No.: 14/943,904

(22) Filed: Nov. 17, 2015

(65) Prior Publication Data

US 2016/0166324 A1 Jun. 16, 2016

Related U.S. Application Data

(60) Provisional application No. 62/091,382, filed on Dec. 12, 2014.

(51) Int. Cl.
| | |
|---|---|
| *A61B 90/11* | (2016.01) |
| *A61B 19/00* | (2006.01) |
| *A61B 17/00* | (2006.01) |

(52) U.S. Cl.
CPC .......... *A61B 19/201* (2013.01); *A61B 90/11* (2016.02); *A61B 2017/00477* (2013.01)

(58) Field of Classification Search
CPC .............................. A61B 90/10; A61B 90/11
See application file for complete search history.

(56) References Cited

U.S. PATENT DOCUMENTS

| 4,592,352 A | 6/1986 | Patil | |
|---|---|---|---|
| 5,116,344 A | 5/1992 | Sundqvist | |
| 5,163,430 A * | 11/1992 | Carol | A61B 90/11 378/20 |
| 5,280,427 A * | 1/1994 | Magnusson | A61B 90/11 600/407 |
| 5,665,095 A * | 9/1997 | Jacobson | A61B 90/11 604/116 |

(Continued)

OTHER PUBLICATIONS

International Search Report and Written Opinion of the International Searching Authority (Forms PCT/ISA/220, PCT/ISA/210 and PCT/ISA/237) for International Application No. PCT/EP2014/077817, dated Jul. 28, 2015.

*Primary Examiner* — Alexander J Orkin
(74) *Attorney, Agent, or Firm* — Birch, Stewart, Kolasch & Birch, LLP

(57) ABSTRACT

A stereotactic surgical instrument for use in stereotactical therapy and surgery and a coupling mechanism for such an instrument is disclosed. The stereotactic surgical instrument includes a semi-circular arc part and a head frame. The head frame is arranged for fixation to a head of a patient by pins or screws. The arc part includes coupling members shaped as rings arranged at a fixed distance from each other for attaching and locking the arc part to the head frame. The head frame includes support members formed as rings for receiving corresponding coupling members. Each coupling member includes a pivotable clamp element arranged to partly surround a respective support member circumferentially when the arc part is coupled to the head frame. The coupling members include locking elements arranged to receive a tip portion of the respective clamp element and adjustable locking knobs for tightening and locking respective coupling member to respective support member.

20 Claims, 4 Drawing Sheets

(56) References Cited

U.S. PATENT DOCUMENTS

| | | | | |
|---|---|---|---|---|
| 5,984,930 A | * | 11/1999 | MacIunas | A61B 90/11 600/417 |
| 2001/0053879 A1 | * | 12/2001 | Mills | A61B 90/11 600/417 |
| 2002/0007188 A1 | * | 1/2002 | Arambula | A61B 17/1757 606/130 |
| 2002/0161446 A1 | * | 10/2002 | Bryan | A61B 17/02 623/17.15 |
| 2003/0208187 A1 | * | 11/2003 | Layer | A61B 90/11 606/1 |
| 2005/0234435 A1 | | 10/2005 | Layer | |
| 2010/0042111 A1 | * | 2/2010 | Qureshi | F16M 11/14 606/130 |

\* cited by examiner

STEREOTACTIC SURGICAL INSTRUMENT

CROSS REFERENCE TO RELATED APPLICATIONS

This non-provisional application claims the benefit under 35 U.S.C. § 119(e) to U.S. Provisional Application No. 62/091,382, filed on Dec. 12, 2014, the entire contents are hereby incorporated by reference into the present application.

FIELD OF THE INVENTION

The present invention relates to the field of stereotactical therapy and surgery. In particular, the invention concerns a stereotactic surgical instrument for use in stereotactical therapy and surgery and a coupling mechanism for such an instrument.

BACKGROUND OF THE INVENTION

Typically during neurological procedures, stereotactic guidance is employed by a physician to reach a target site. Stereotactic guidance is generally defined as the ability to locate and access on object in a three-dimensional space. Further, surgical delivery by an instrument is often guided by use of three-dimensional scanning technique such as computed tomography (CT) or magnetic resonance imaging (MRI). Typically, such stereotactic procedures require the use of a stereotactic head frame, which is generally referred to as a frame-based stereotaxy procedure. A typical stereotactic head frame is a halo-like or ring-like device that is rigidly affixed to the patient's skull by means of pins or screws. A semi-circular arc for holding an instrument is attached to the head frame.

When the head frame is fixed or secured, the head frame is used to define a target and a trajectory to the target. This can be achieved, for example, with use of CT or MRI images. The head frame may also be used as a guide for delivering various types of instruments, such as a biopsy needle or DBS (Deep Brain Stimulation) leads or electrodes.

In order to correct positioning and adjustment of the head frame and the semi-circular arc, the head frame and arc typically include graduations or indentations that are scaled to provide separate discreet movements along the scale of the head frame and arc. This requires knowledge and long experience by the user. The target and trajectory adjustments and positioning is manually adjusted via adjustment knobs arranged on the head frame and these manual adjustments of the various scales to adjust the x, y, and z coordinates, as well as the rotations about these coordinates for targeting and trajectory are susceptible for human error and are time consuming. Particularly, the steps of attaching the arc to the support members of the head frame and adjusting the x coordinate after attachment of the arc to the head frame via the support members are difficult and cumbersome and also require experience and are therefore time consuming and susceptible for human error.

It is therefore a need to provide a stereotactic surgical instrument where the mounting or attachment of the arc to the head frame is facilitated and also in a manner that is accurate and precise in line with the high demands on tolerance and precision in such an environment.

SUMMARY OF THE INVENTION

An object of the present invention is to provide a stereotactic surgical instrument where the mounting or attachment of the arc to the support members of the head frame is facilitated.

Another object of the present invention is to provide a stereotactic surgical instrument that is accurate and precise in line with the high demands on tolerance and precision in a surgical and clinical environment.

This and other objects are achieved by providing a calibration method having the features defined in the independent claim. Preferred embodiments are defined in the dependent claims.

According to an aspect of the present invention, there is provided a stereotactic surgical instrument including a semi-circular arc part and a head frame, wherein the head frame is arranged for fixation to a head of a patient by means of pins or screws, wherein the arc part comprises coupling members shaped as rings arranged at a fixed distance from each other for attaching and locking the arc part to the head frame, wherein the head frame comprises support members formed as rings for receiving corresponding coupling members, wherein each coupling member includes a pivotable clamp element arranged to partly surround a respective support member circumferentially when the arc part is coupled to the head frame, and wherein the coupling members includes locking elements arranged to receive a tip portion of the respective clamp element and adjustable locking knobs for tightening and locking respective coupling member to respective support member.

According to a second aspect of the present invention, there is provided a coupling mechanism for coupling or attaching a semi-circular arc part rigidly to a head frame of a stereotactic surgical instrument for use in stereotactic surgery, wherein the head frame is arranged for fixation to a head of a patient by means of pins or screws, wherein the arc part comprises coupling members shaped as rings arranged at a fixed distance from each other for locking the arc part to the head frame, wherein the head frame comprises support members formed as rings for receiving corresponding coupling members, wherein each coupling member includes a pivotable clamp element arranged to partly surround a respective support member circumferentially when the arc part is coupled to the head frame, and wherein the coupling members includes locking elements arranged to receive a tip portion of the respective clamp element and adjustable locking knobs for tightening and locking respective coupling member to respective support member.

The present invention is based on the idea that mounting and adjustment of an arc part of a stereotactic surgical instrument to a head frame of the stereotactic surgical instrument, where the head frame is fixed to patient's head, can be significantly facilitated by providing a support members on the head frame and corresponding coupling members on the art fixed relative each other. That is, the coupling members of the arc part and the support members of the head frame are arranged at fixed X-coordinate. Thereby, the need of adjusting the X-coordinate after the arc is attached to the head frame is eliminated. This has been enabled by the new and inventive coupling mechanism of according to the present invention including ring-like support members arranged on the head frame and corresponding ring-like coupling members of the arc part that allows a connection between these ring-like members by a radial sliding along corresponding ring planes. Further, the coupling members comprise pivotable clamp element, for example, shaped as semi-circles or rings designed to co-operate with and partly surround a respective support member circumferentially when the arc part is coupled to the head frame. This facilitates to connection of the art to the head frame.

In preferred embodiments of the present invention, each pivotable clamp element comprises a nose part arranged to co-operate with a respective support member so as to close the clamp element about the support member when pressed against each other. This entails an easy and fast attachment of the coupling members to the corresponding support members. In embodiments of the present invention, the nose part is provided with a curved section to co-operate with the corresponding support member. In further embodiments, the curved section co-operates with a guiding section or step of the corresponding support member.

In preferred embodiments of the present invention, each support member comprises a guiding part formed as a circular projecting part extending in a circumferential direction on an outer surface of the support member, wherein the guiding part is arranged to receive the nose part of a respective coupling member.

According to embodiments of the present invention, the guiding part includes a circular ridge extending in a circumferential direction, wherein said ridge comprises an oblique section, and a recess extending in the circumferential direction.

According to embodiments of the present invention, the clamp element includes a circular ridge extending in a circumferential direction, wherein said ridge comprises an oblique section, and a recess extending in the circumferential direction.

According to embodiments of the present invention, the ridge and recess of the clamp element are arranged to mate with corresponding with recess and ridge of the support member.

According to an embodiment of the present invention, wherein the arc part comprises two coupling members fixated to the arc part at a fixed distance from each other.

As readily understood by the person skilled in the art, various known methods for determining the radiation focus point could be used, of which some have been described above. However, the present invention is not restricted to the particular examples shown and described herein, but any suitable measurement method for determining the radiation focus point is contemplated within the scope of the present invention.

BRIEF DESCRIPTION OF THE DRAWINGS

Preferred embodiments of the invention will now be described in greater detail with reference to the accompanying drawings, in which FIG. 1 schematically illustrates an overview of a stereotactic system in which the present invention can be used.

DESCRIPTION OF PREFERRED EMBODIMENTS

The following description of the embodiment(s) according to the present invention is merely exemplary and is not intended to limit the invention, its application, or uses.

Moreover, while the present invention is discussed in detail below with reference to deep brain stimulation (DBS), the present invention for use in stereotactic surgery may be utilized for any type of neurological procedure or instrument, including biopsy needles, cannulas, catheters, implants guide wires, needles and styles and may also be used for delivery of electricity, drugs, genes or cells, as well as for ablation of, for example, vascular blockage or tumors or any other neurological intervention in the brain.

Figure 1:
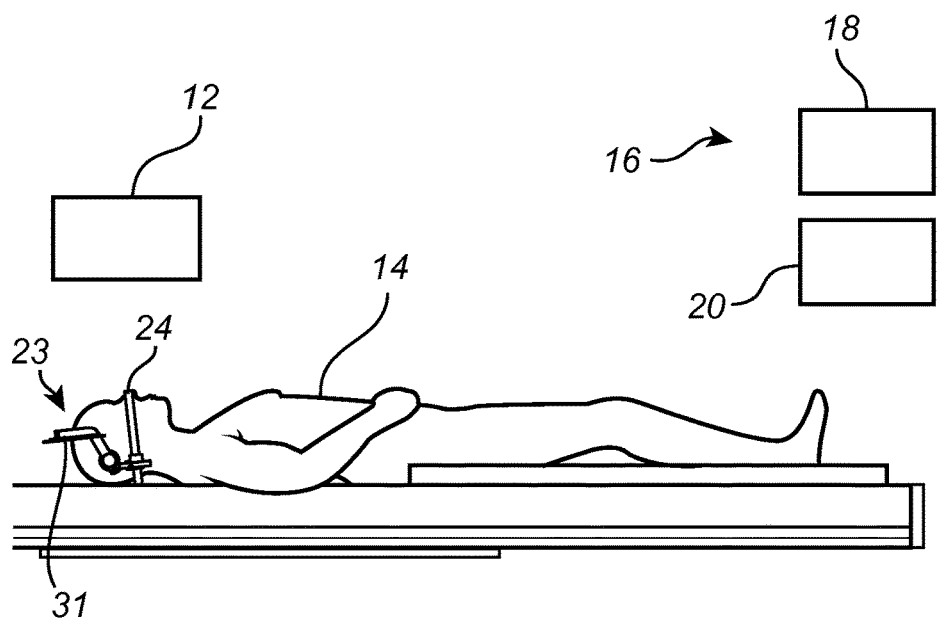

With reference to FIG. 1, an overview of an exemplary stereotactic surgery system in which the present invention may be used. The stereotactic system 10 may include an optional imaging device 12 that is used to acquire images, e.g. in real-time or pre-operative, of the patient 14. The imaging device 12 may include a MRI imaging system and/or a CT imaging system.

The imaging system 12 may be controlled by a user from a controller, computer or work station 16 having a display 18 and a user interface 20. The work station 16 provides facilities for displaying on the display 18, saving, digitally manipulating, or printing a hard-copy of, for example, images from the imaging device 12 and from the pre-operative scans.

The user interface 20 may be a mouse, a keyboard, touch pen, touch screen or other suitable device that allows a physician or user to provide inputs to control the imaging device 12.

A stereotactic surgical instrument 23 is used for the invasive procedure including a stereotactic head frame 24 fixed to the patient's head and a semi-circular arc part 31 for holding the surgical instrument. The arc part 31 is attached to the head frame 24 in a fixed position relative the head frame 24 and the patient 14.

Figure 2:
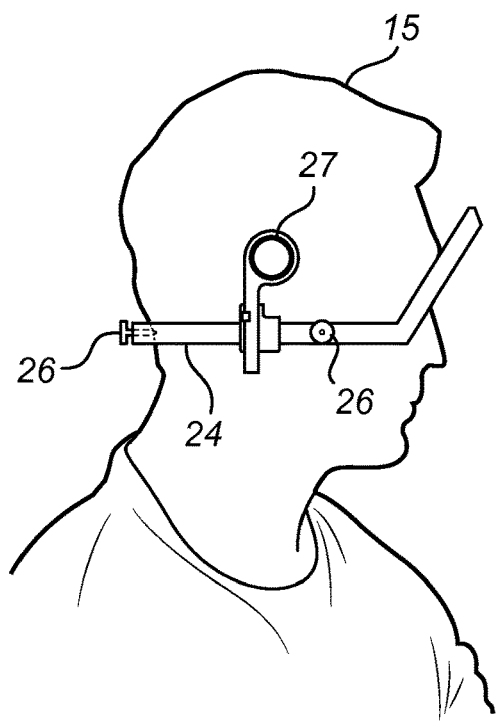
FIG. 2 schematically illustrates a head frame of a stereotactic surgical instrument according to the present invention.

The stereotactic head frame 24, as schematically shown in FIG. 2, is usually fixed to the patient's 14 scull or head 15 via pins or screws 26. The head frame 24 generally includes a ring-like structure or frame 25 for fixation to the head via the screws 26 and support members 27 for attachment of the semi-circular arc 28 (see e.g. FIGS. 3a-3c and 4) to the head frame 24. According to preferred embodiments of the present invention, the support members 27 of the coupling mechanism 30 are formed as rings with a guiding part, section or surface 37 formed as circular a projecting part or section having a smaller outer diameter than the ring 27 and having a circumferential extension.

The arc part 28 comprises coupling members 31 shaped as rings for fitting and locking the arc part 28 to the head frame 24 at the support members 27 for receiving corresponding coupling members 31.

Each coupling member 31 includes a pivotable clamp element 32 arranged to partly surround a respective support member 27 circumferentially when the arc part 28 is coupled to the head frame 24. This is illustrated in FIGS. 3a-3c.

Figure 3A:
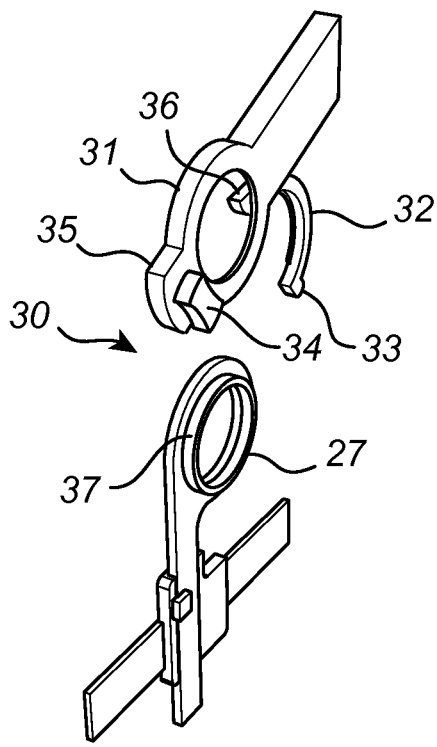
FIG. 3a-3c schematically illustrates an attachment procedure for attaching the semi-circular arc to the head frame.
Figure 3B:
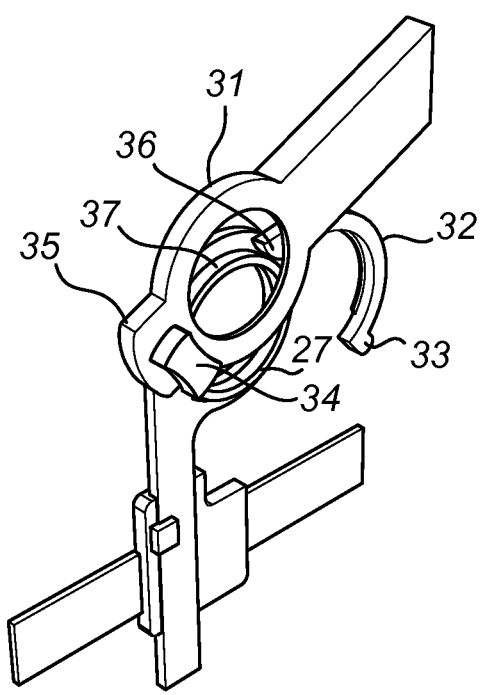
Figure 3C:
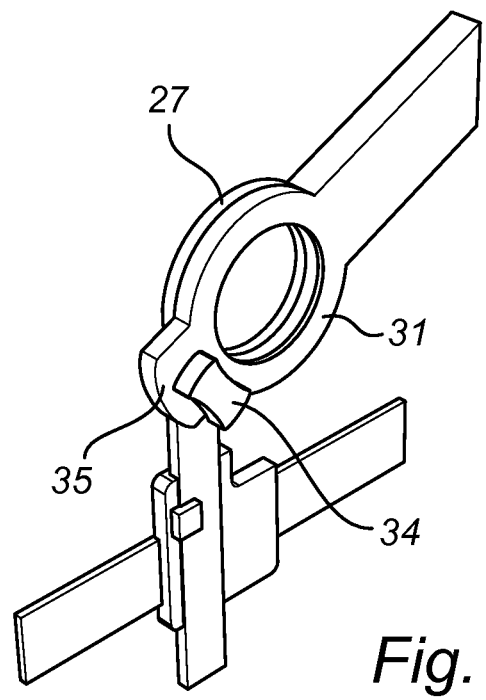
Figure 4:
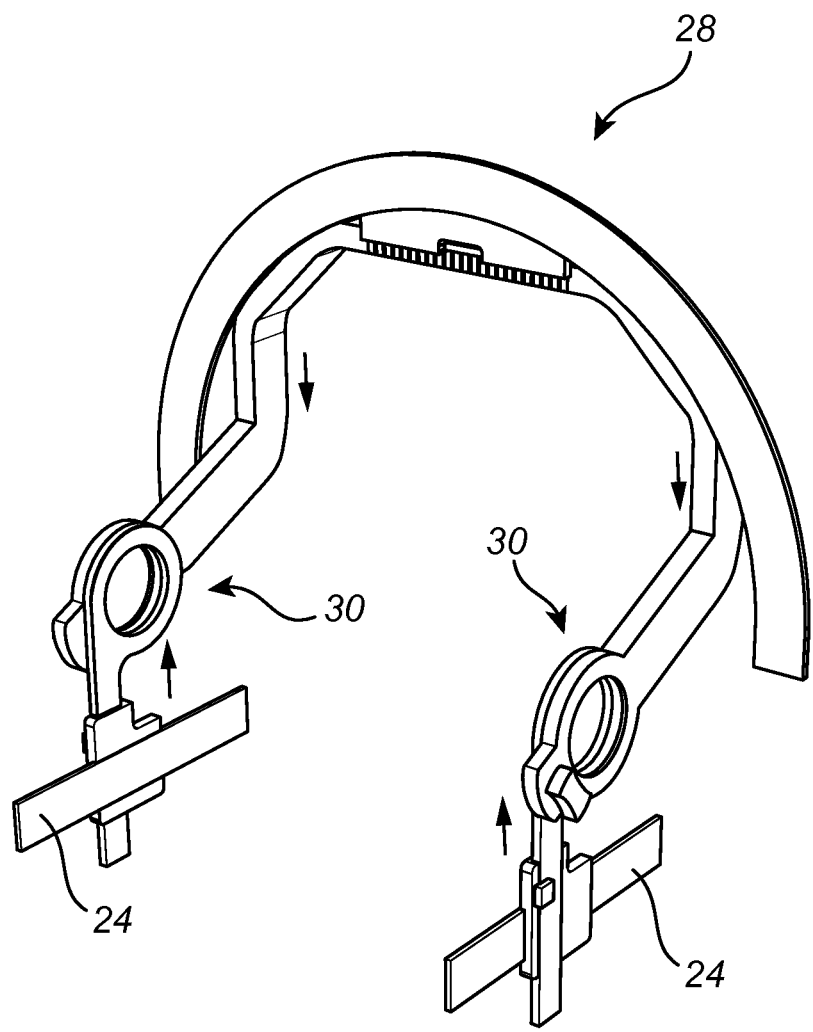
FIG. 4 schematically illustrates the stereotactic surgical instrument according to the present invention.

In FIG. 3a, the arc part 28 is moved towards the head frame 24 such that respective coupling member 31 is aligned with corresponding support member 27. As illustrated in FIGS. 3b and 3c, a nose part 36 provided on respective clamp element 32 is arranged to co-operate with the corresponding support member 27 so as to close the clamp element 32 about the support member 27. As the coupling members 31 and the corresponding support members are connected, the support members 27 and the corresponding coupling member lock by sliding radially along the ring planes. The clamp elements 32 close the coupling member 31. When the clamp elements 32 has closed around respective support member 27 as shown in FIG. 3c, the arc part 28 is pivotally fixed to the head frame 24. The arc part 28 can be pivoted in an arc like manner relative the head frame 24 so as to adjust a rotational angle, i.e. a position of the arc part 28 relative the head frame 24. In embodiments of the present invention, the coupling members 31 are provided with a scaling in order to enable an accurate and easy adjustment of the rotational angle.

Further, coupling members 31 includes locking elements 35 arranged to receive a tip portion 33 of the respective clamp element 32 and adjustable locking knobs 34 for tightening and locking respective coupling member 31 to respective support member 27. Hence, the coupling members 31 can be locked in a fixed position relative the corresponding support members 27.

Figure 5:
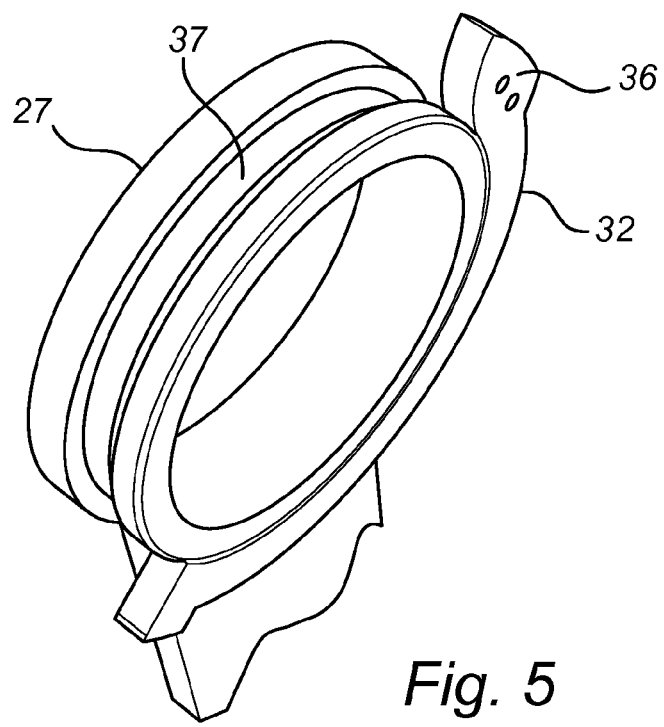
FIG. 5 schematically illustrates a detailed view of the support member and coupling member when coupled to each other.

In FIG. 5 another detailed view of the support member 27 when coupled to a coupling member 31 is shown.

Figure 6:
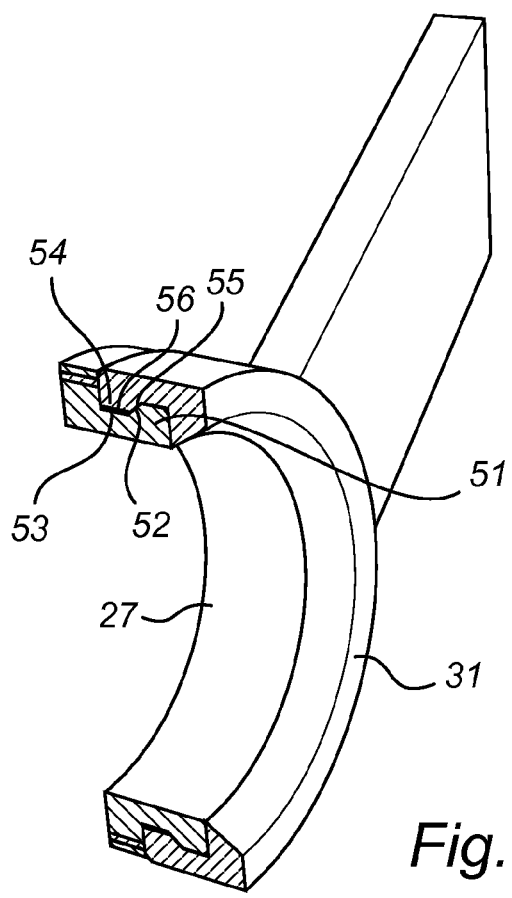
FIG. 6 schematically illustrates a cross-sectional view of the support member and coupling member when coupled to each other.

In FIG. 6, a cross-sectional view of the support member 27 and the coupling member 31 when coupled to each other is shown. The guiding part 37 of the support member 27 includes a circular ridge 51 extending in a circumferential direction, wherein the ridge 51 comprises an oblique section 52, and a recess 53 extending in the circumferential direction. Further, the clamp element 32 includes a circular ridge 54 extending in a circumferential direction, wherein the ridge 54 comprises an oblique section 55, and a recess 56 extending in the circumferential direction. As can be seen, the ridge 54 and recess 56 of the clamp element 32 are arranged to mate with corresponding with recess 53 and ridge 51 of the support member 27.

Even though the present invention has been described above using exemplifying embodiments thereof, alterations, modifications, and combinations thereof, as understood by those skilled in the art, may be made without departing from the scope of the invention as defined in the accompanying claims.

The invention claimed is:

1. A stereotactic surgical instrument comprising:
   a semi-circular arc defined by first and second ends configured to be positioned on opposite sides of a patient; and
   a head frame configured to encompass a head of the patient,
   wherein the head frame is arranged for fixation to the head of the patient by pins or screws,
   wherein the first and second ends of the arc comprise coupling members shaped as rings for attaching and locking the arc directly to the head frame,
   wherein the head frame comprises support members formed as rings for receiving corresponding coupling members,
   wherein each coupling member includes a pivotable clamp element arranged to partly surround a respective support member circumferentially when the arc is coupled to the head frame, and
   wherein the coupling members include locking elements arranged to receive a tip portion of the respective clamp element and adjustable locking knobs for tightening and locking a respective coupling member to a respective support member, such that the arc is pivotally fixed to the head frame and can be pivoted in an arc manner to adjust a rotational angle of the arc, where the coupling members enable adjusting and locking of the rotational angle of the arc.

2. The stereotactic surgical instrument according to claim 1, wherein each pivotable clamp element comprises a nose part arranged to co-operate with a respective support member so as to close the clamp element about the support member.

3. The stereotactic surgical instrument according to claim 2, wherein the arc comprises two coupling members fixated to the arc at a fixed distance from each other.

4. The stereotactic surgical instrument according claim 2, wherein each support member comprises a guiding part formed as a circular projecting part extending in a circumferential direction, and wherein the guiding part is arranged to receive the nose part of a respective coupling member.

5. The stereotactic surgical instrument according to claim 4, wherein the arc comprises two coupling members fixated to the arc at a fixed distance from each other.

6. The stereotactic surgical instrument according to claim 4, wherein the guiding part includes a circular ridge extending in a circumferential direction, and wherein said ridge comprises an oblique section, and a recess extending in the circumferential direction.

7. The stereotactic surgical instrument according to claim 6, wherein the clamp element includes a circular ridge extending in a circumferential direction, and wherein said ridge comprises an oblique section, and a recess extending in the circumferential direction.

8. The stereotactic surgical instrument according to claim 6, wherein the arc comprises two coupling members fixated to the arc at a fixed distance from each other.

9. The stereotactic surgical instrument according to claim 4, wherein the clamp element includes a circular ridge extending in a circumferential direction, and wherein said ridge comprises an oblique section, and a recess extending in the circumferential direction.

10. The stereotactic surgical instrument according to claim 9, wherein the arc comprises two coupling members fixated to the arc at a fixed distance from each other.

11. The stereotactic surgical instrument according to claim 9, wherein the ridge and recess of the clamp element are arranged to mate with a corresponding recess and ridge of the support member.

12. The stereotactic surgical instrument according to claim 11, wherein the arc comprises two coupling members fixated to the arc at a fixed distance from each other.

13. The stereotactic surgical instrument according to claim 1, wherein the arc comprises two coupling members fixated to the arc at a fixed distance from each other.

14. A coupling mechanism for coupling or attaching a semi-circular arc rigidly to a head frame of a stereotactic surgical instrument for use in stereotactic surgery, wherein the head frame is arranged for fixation to a head of a patient by means of pins or screws and is configured to encompass the head of the patient,
   wherein the semi-circular arc is defined by first and second ends configured to be positioned on opposite sides of the patient,
   wherein the first and second ends of the arc comprise coupling members shaped as rings for locking the arc directly to the head frame,
   wherein the head frame comprises support members formed as rings for receiving corresponding coupling members, wherein each coupling member includes a pivotable clamp element arranged to partly surround a respective support member circumferentially when the arc is coupled to the head frame, and
   wherein the coupling members include locking elements arranged to receive a tip portion of the respective clamp element and adjustable locking knobs for tightening and locking a respective coupling member to a respective support member, such that the arc is pivotally fixed to the head frame and can be pivoted in an arc manner to adjust a rotational angle of the arc, where the coupling members enable adjusting and locking of the rotational angle of the arc.

15. The coupling mechanism according to claim 14, wherein each pivotable clamp element comprises a nose part arranged to co-operate with a respective support member so as to close the clamp element about the support member.

16. The coupling mechanism according claim 15, wherein each support member comprises a guiding part formed as a circular recess on an outer surface of the support member, and wherein the guiding part is arranged to receive the nose part of a respective coupling member.

17. The coupling mechanism according to claim 16, wherein the guiding part includes a circular ridge extending in a circumferential direction, and wherein said ridge comprises an oblique section, and a recess extending in the circumferential direction.

18. The coupling mechanism according to claim 16, wherein the clamp element includes a circular ridge extending in a circumferential direction, and wherein said ridge comprises an oblique section, and a recess extending in the circumferential direction.

19. The coupling mechanism according to claim 18, wherein the ridge and recess of the clamp element are arranged to mate with a corresponding recess and ridge of the support member.

20. The coupling mechanism according to claim 14, wherein the arc comprises two coupling members fixated to the arc at a fixed distance between each other.

\* \* \* \* \*